United States Patent
Brieussel et al.

(10) Patent No.: US 8,123,871 B2
(45) Date of Patent: Feb. 28, 2012

(54) MACHINE FOR WASHING MEDICAL AND/OR SURGICAL INSTRUMENTS

(75) Inventors: Jean-Marie Brieussel, Toulouse (FR); Nathalie Foglieni Guillaud, Frouzins (FR)

(73) Assignee: Lancer Industrie, Tournefeuille (FR)

( * ) Notice: Subject to any disclaimer, the term of this patent is extended or adjusted under 35 U.S.C. 154(b) by 587 days.

(21) Appl. No.: 12/439,925

(22) PCT Filed: Aug. 29, 2007

(86) PCT No.: PCT/FR2007/001409
§ 371 (c)(1),
(2), (4) Date: Mar. 4, 2009

(87) PCT Pub. No.: WO2008/029012
PCT Pub. Date: Mar. 13, 2008

(65) Prior Publication Data
US 2010/0300497 A1 Dec. 2, 2010

(30) Foreign Application Priority Data
Sep. 8, 2006 (FR) .................................... 06 07880

(51) Int. Cl.
*B08B 3/00* (2006.01)
(52) U.S. Cl. .......... 134/115 R; 49/192; 49/193; 16/231; 16/232
(58) Field of Classification Search ............ 16/366, 16/137
See application file for complete search history.

(56) References Cited

U.S. PATENT DOCUMENTS

| 4,042,805 A | 8/1977 | Kopacz |
| 6,282,838 B1 * | 9/2001 | Yoshikawa ................. 49/193 |
| 2007/0181162 A1 | 8/2007 | Classen et al. |

FOREIGN PATENT DOCUMENTS

| BE | 644545 | 6/1964 |
| DE | 32 40 284 | 5/1984 |
| EP | 1 340 512 | 9/2003 |
| FR | 2 806 286 | 9/2001 |
| FR | 2 843 028 | 2/2004 |
| WO | 2006/015934 | 2/2006 |

OTHER PUBLICATIONS

International Search Report dated Dec. 12, 2008, from corresponding PCT application.

* cited by examiner

*Primary Examiner* — Michael Barr
*Assistant Examiner* — Caitlin N Dennis
(74) *Attorney, Agent, or Firm* — Young & Thompson

(57) ABSTRACT

A machine for washing surgical and/or medical instruments (1), includes a washing tank (2) designed to receive surgical and/or medical instruments (1) and a door (4) positioned facing the tank (2) so that it can be used to seal the tank or provide access thereto. The door (4) is mounted to a bilateral hinge designed to enable the door to be opened: to a first loading position on the loading side (5) of the machine, in order to provide access to the tank on the loading side (5) and prevent the tank from being accessed on the other side; and to a second unloading position on the opposite unloading side (6) of the machine, in order to provide access to the tank on the opposite unloading side (6) and prevent the tank from being accessed on the loading side (5).

19 Claims, 5 Drawing Sheets

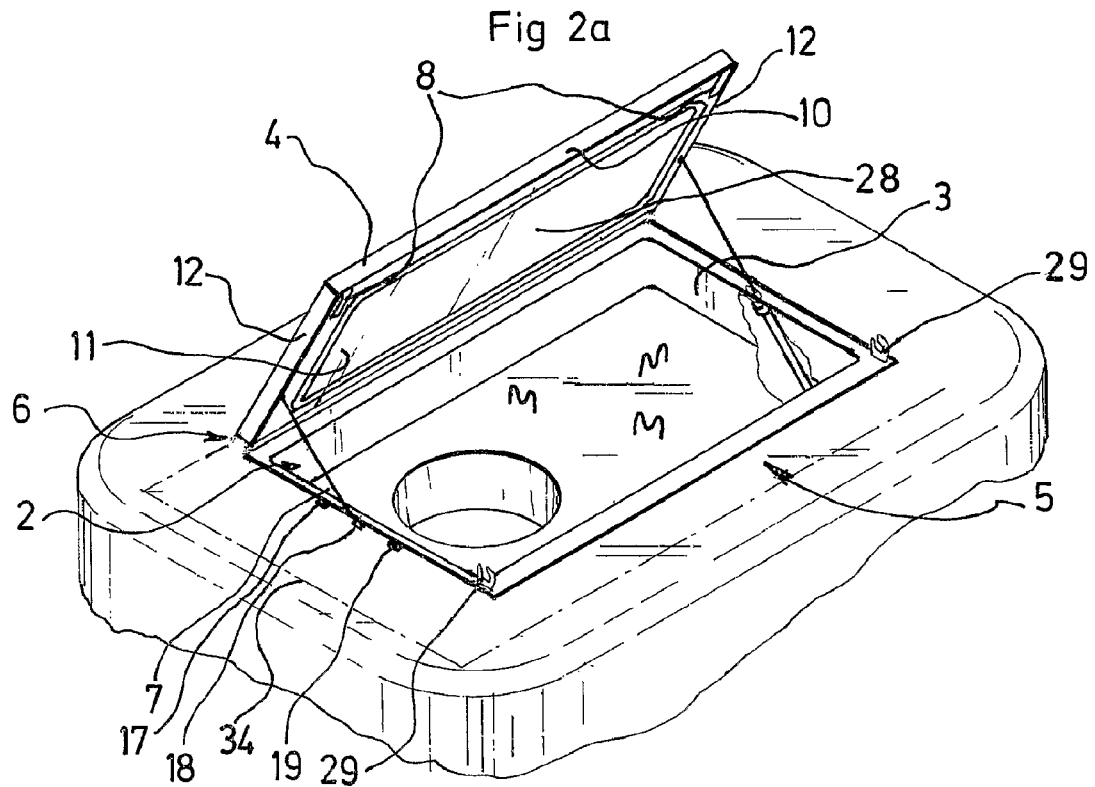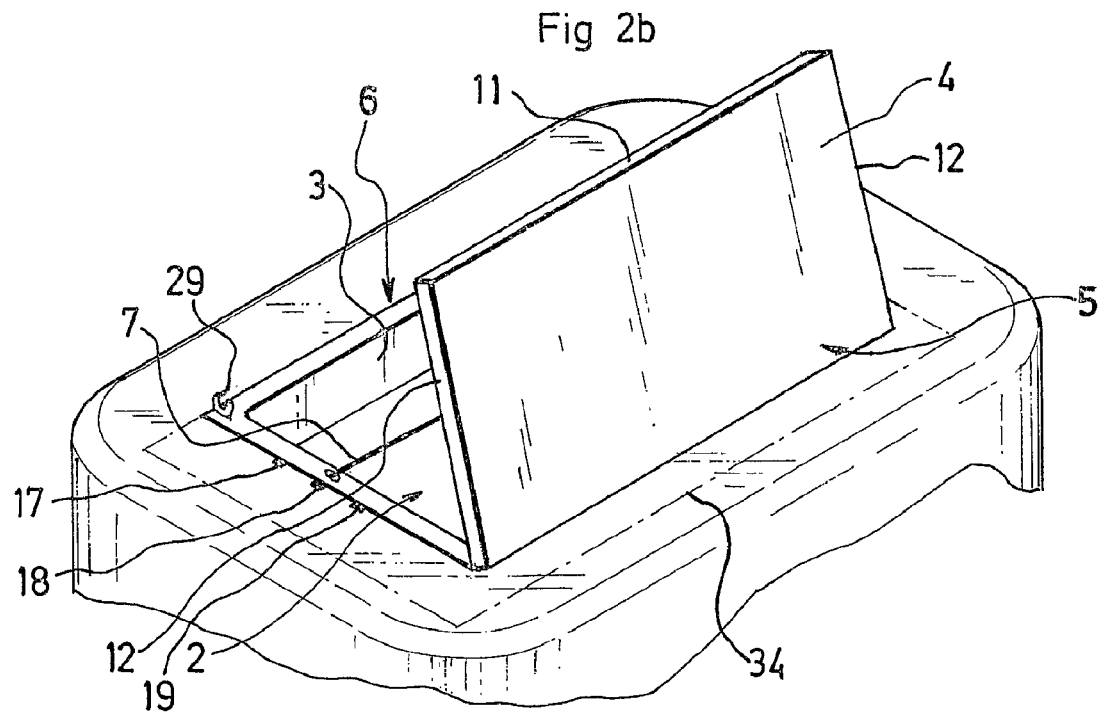

MACHINE FOR WASHING MEDICAL AND/OR SURGICAL INSTRUMENTS

Figure 1:
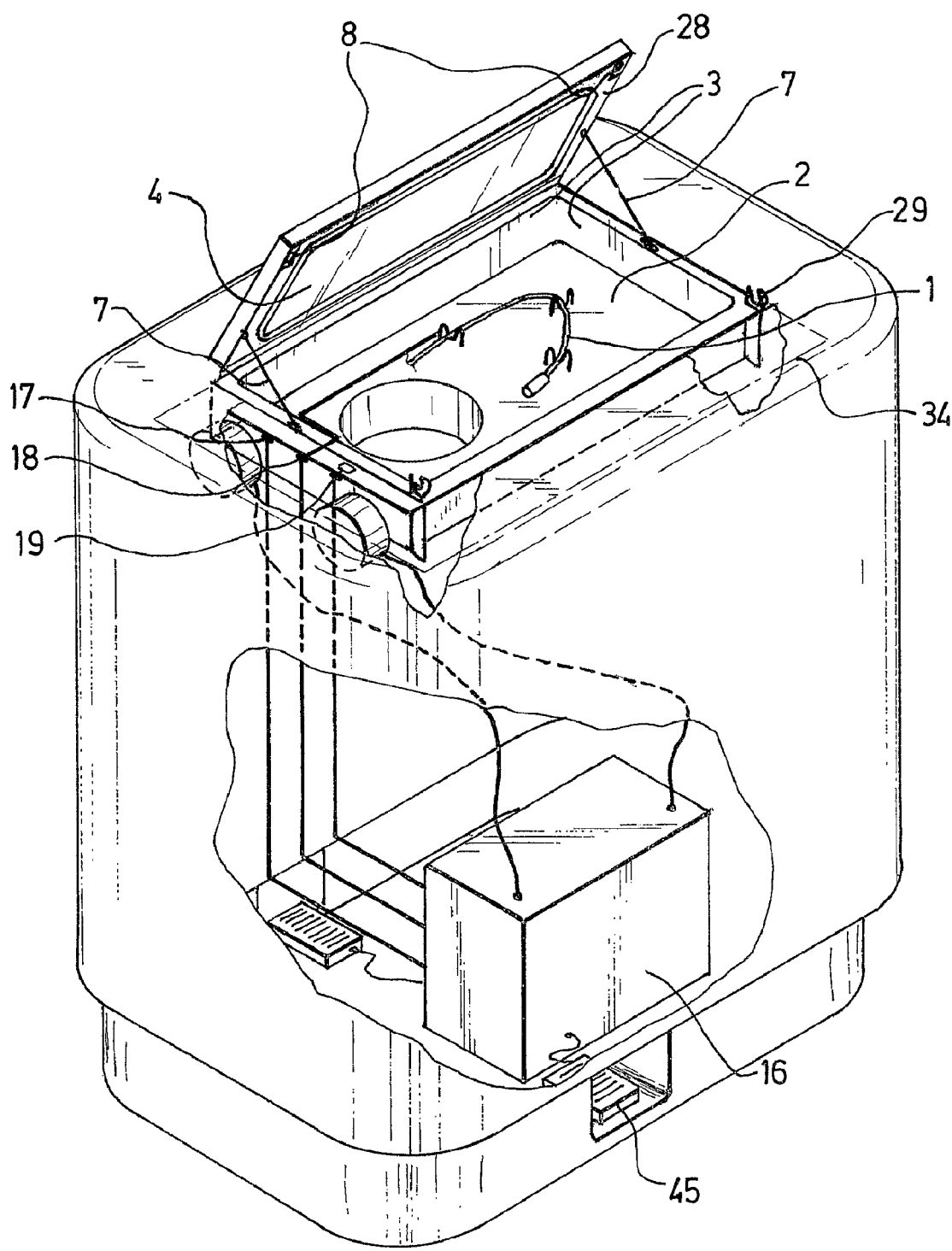

The invention relates to a machine for washing medical and/or surgical instruments, such as fibroscopes, endoscopes, echocardiographic probes, echographic probes and any other instrument requiring washing before each use.

Said medical and/or surgical instruments require meticulous and systematic washing before each use so as to prevent any risk of contamination of a patient on which said instruments are to be used. Typically, such washing cleans, rinses, disinfects and dries the inside and outside of the devices so as to eliminate organic matter (blood, feces, respiratory secretions, etc.) and germs possibly present on, or in, said devices.

Numerous disinfecting washing machines exist for washing instruments for medical and/or surgical use.

Machines for washing/disinfecting form the subject of stringent regulations concerning, in particular, their type and their use. In particular, the regulations EN ISO 15883-1, 15883-2, 15883-3, 15883-4 and 15883-5 require the implementation of traceability means which make it possible to indicate clearly if the cycle has completely finished or not, in order to authorize or not the use of the treated instruments. The machines also have to be provided with a system for locking the door which prevents access to the load (instrument) during the treatment cycle. Generally, it is possible to stop the treatment cycle before it has finished and thus access the load. However, in this case, the treatment cycle is not validated and the instruments have to undergo a further treatment cycle.

Throughout the text, unless indicated to the contrary, the terms "washing", "to wash" and their derivations refer to any treatment comprising at least one step carried out on all or part of an instrument, on the outside and/or on the inside of an instrument and selected from the group formed by the steps of: precleaning (pre-rinse); cleaning (mechanical and/or by chemical solution); rinsing; disinfection; sterilization; blowing; drying.

Two known configurations of machines for washing medical and/or surgical instruments exist:
- machines provided with a single door for loading/unloading the instruments (cf. for example FR 2806286);
- machines provided with two separate doors for each washing tank, one for loading the instruments to be washed, the other for unloading the washed instruments; said machines are positioned in a passage through a partition with the loading door opening on one side of the partition into a "dirty" zone (for example a room for prewashing and for loading a plurality of washing machines), whilst the unloading door opens on the other side of the partition into a "clean" zone (for example a room for packaging washed instruments and/or for loading sterilizing autoclaves for thermoresistant instruments).

The machines for washing medical and/or surgical instruments are generally also provided with automatic controls which govern the opening and closing of the door or doors. For example, in the case of machines provided with two doors, in the event of stopping the treatment cycle before the end, access to the load of the machine may only be made from the loading door side.

Machines provided with two separate doors per tank provide greater operational safety, to the extent that the washed instruments never circulate in a space in which the unwashed instruments are also able to circulate. Said machines thus permit, in particular, the implementation of the principle known as the "forward movement" principle, making it possible to prevent the washed instruments from being able to come into contact with the unwashed instruments at any point of the cycle for storing, use or treatment of the instruments. Nevertheless, said machines designed to be arranged in a passage through a partition have the drawbacks of high cost, a significant spatial requirement and requiring an infrastructure and logistics specific to their implementation (two different rooms, arrangements of the machine in a passage through a partition, duplication of personnel, etc.).

In this context, the object of the invention is to provide a machine for washing medical and/or surgical instruments which have the combined advantages of the known machines provided with a single door and the known machines with two doors, without nevertheless having the drawbacks of either.

The object of the invention is, in particular, to propose such a machine which permits the implementation of the "forward movement" principle whilst having a similar cost to that of a known machine with a single door, and less than that of machines with two separate doors per tank, both as regards the cost of manufacturing the machine itself and that associated with the installation and the use thereof.

The object of the invention is also to propose such a machine which is capable, without physically altering the machine itself and by simply modifying a recorded parameter, of making this machine operate either with access on two separate sides of the machine, or with access on a single side of the machine, so as to permit in this manner a high degree of flexibility of use and increased operation of the machine.

The object of the invention is also to propose such a machine which has increased operational safety, in particular with regard to the risks of contamination during the loading/unloading operations.

To achieve this, the invention relates to a machine for washing medical and/or surgical instruments, comprising:
- at least one washing tank designed to receive medical and/or surgical instruments, said tank being defined by walls and comprising an opening for access to the tank for loading instruments to be washed into the tank or unloading the washed instruments from the tank,
- a door arranged opposite said opening of said washing tank, said door being mounted on the machine so as to be able to pass from one position, known as the washing position, in which it sealingly covers said opening of said washing tank so as to permit a washing cycle, into at least one position, known as the open position, in which it permits access to the washing tank to load the instruments to be washed and/or to unload the washed instruments, wherein said door is mounted on a hinge, known as a bilateral hinge, designed to allow a first lateral opening of the door, known as the opening for loading, on a first side, known as the loading side for the tank of the machine, in which said door permits access to said tank from said loading side of the tank and prevents access to said tank from the opposing side, and to permit a second lateral opening, known as the opening for unloading, on the opposing side, known as the unloading side of the tank of the washing machine, in which said door permits access to said tank from said unloading side and prevents access to the tank from said loading side.

A washing machine according to the invention comprises, for each tank, a single access opening and a single door. In one advantageous embodiment, the machine is provided with a single tank, and thus with a single loading and unloading door. There is nothing, however, to prevent the manufacture of a single machine bringing together a plurality of washing tanks, each tank being provided with a single loading/unloading door. In this variant, all the openings of the doors are oriented on the same loading side of the machine and all the openings for unloading are oriented on the same opposing side for unloading the machine.

For each washing tank, the door mounted on a bilateral hinge according to the invention makes it possible to define a tank loading side—in particular of the machine—and a tank unloading side—in particular of the machine. Moreover, a bilateral hinge permits a bilateral opening of the door which permits access to the tank on the open side and prevents access to the tank on the opposing side. Henceforth, a machine according to the invention may be arranged, for example, between an operating room and a preparation room, the loading side being accessible from the preparation room and the unloading side being accessible from the operating room. In this manner, any instrument accessible to the surgeon in the operating room has to be a clean instrument which has undergone a washing cycle. If the washing cycle has not been carried out, the door may not be opened on the unloading side. It is noteworthy, moreover, that this safe access is obtained with a single door, and thus with a less costly machine than a known machine provided with two separate doors per tank, and without even requiring a heavy infrastructure. For example, a machine according to the invention may be used with a high degree of operational safety according to the principle known as the "forward movement" principle, but without needing to be placed in a passage through a partition. More specifically, the bilateral hinge of the door makes it possible to avoid any errors when said door is open and the door itself constitutes, in the open position, a separation between the clean and dirty zones. There is nothing to prevent, however, a machine according to the invention from being positioned in the region of a passage through a partition.

Advantageously, a machine according to the invention is also characterized in that it comprises:
  means for locking, in at least two states of said door, a locked state in which said locking means are designed to lock said door in the washing position such that it is impossible to open said door during a washing cycle, and an unlocked state in which said locking means are designed to allow an opening of said door,
  a control unit for said locking means designed to control the locking and unlocking of the locking means.

A washing machine according to the invention provided with locking means and a control unit for said locking means makes it possible to ensure accurate control of the washing cycles. In particular, a washing machine according to the invention may guarantee that the access to the tank of the machine is only possible when a washing cycle has been carried out. Moreover, a washing machine according to the invention, provided with a control unit, may require the locking of the locking means so as to prevent access to the tank as soon as the door is closed and to allow the unlocking of the locking means, in particular if a successful washing cycle has taken place.

Advantageously, a control unit according to the invention is also designed to interrupt, as required by an operator, a washing cycle which is underway. In this case, the control unit only authorizes an opening of the door on the loading side of the machine.

A control unit according to the invention may be of any known type. Such a control unit may comprise means for programming said control unit. Such a control unit may comprise analogue means or digital means or a combination of analogue means and digital means.

Advantageously, a washing machine according to the invention comprises, associated with the control unit:

at least one positioning sensor for said door, known as a door sensor, designed to detect an open position of said door and a closed position of said door,
  at least one sensor for detecting the presence of medical and/or surgical instruments in said tank, known as the tank sensor,
  at least one washing indicator in two states, a washed state corresponding to the end of the washing cycle, and a state to be washed, corresponding to a washing cycle to be carried out or underway.

A washing machine provided with such sensors makes it possible to ensure accurate control of the washing cycles. In particular, in a washing machine according to the invention, the control unit receives and utilizes information relative to the position of the door, the state of a washing cycle and the contents of the washing tank and thus ensures rigorous control and monitoring operations.

Advantageously and according to the invention, said control unit is designed to:
  control the locking of said locking means if at least said door sensor detects a closed door, said tank sensor detects instruments in said tank and said washing indicator indicates said state to be washed,
  control the unlocking of said locking means in the other cases.

Such a door locking control which is subject to a combination of at least three conditions—door closed, instruments in the tank and indicator in the state to be washed—makes it possible, on the one hand, to guarantee, in normal operation, that the door may not be opened during a washing cycle or as long as a washing cycle has not been carried out, and makes it possible, on the other hand, to allow an opening of the door in all other cases. In particular, if the washing cycle is in the washed state and instruments are present in the tank, it is then possible to open and close the door without causing the locking of the door. In contrast, as soon as the instruments are unloaded from the machine, the tank sensor indicates an absence of instruments.

Also, advantageously and according to the invention, said control unit is designed to change the state of said washing indicator from the washed state to the state to be washed as soon as said tank sensor no longer detects instruments in said washing tank. Moreover, the control unit is also designed to allow the interruption of a washing cycle which is underway, before the end of said washing cycle and only to allow the opening of the door on the loading side.

Henceforth, a washing machine according to the invention considerably reduces the risks of confusion between a dirty instrument and a clean instrument.

A control unit according to the invention associated with sensors according to the invention makes it possible to prevent clean instruments from coming into contact with dirty instruments.

In the case of a machine with a plurality of washing tanks, the same control unit may be designed to control the operation of the different tanks, in a synchronous or asynchronous manner.

Advantageously and according to the invention, said locking means comprise three states, a locked state in which they are designed to lock said door in the washing position, a first unlocked state, known as the unlocked loading state in which they are designed to permit an opening of said door for loading, and a second unlocked state known as the unlocked unloading state, in which they are designed to permit the opening of said door for unloading.

Advantageously and according to the invention, said control unit is designed to:

control the passage of the locking means into the unlocked loading state if at least said presence sensor detects an absence of instruments for washing and a door sensor detects a closed door, control the passage of the locking means into the unlocked unloading state if at least said washing indicator indicates said washed state and a door sensor detects a closed door.

Thus, if the door sensor detects a closed door, the associated control unit is designed to control the passage of the locking means into the unlocked loading state if no instrument is present in the tank, so as to be able to reload the machine with instruments to be washed. This takes place, in particular, when, after having removed the clean equipment from the machine, the door thereof is reclosed. Moreover, according to this variant of the invention, if the door sensor detects a closed door, the control unit is designed to control the passage of the locking means into the unlocked unloading state if the washing indicator indicates the washed state, so as to be able to remove the washed instruments and to use them.

In contrast, whilst the door is open, on the loading side or on the unloading side, the state of the locking means may not be changed. From an open position, for loading or unloading, only a detection of the closed door may allow a change of the state of the locking means.

Advantageously, a washing machine according to the invention comprises a pedal, known as the unloading pedal, arranged on the unloading side of the machine and designed to activate an opening of the door of the machine for unloading, and a pedal, known as the loading pedal, arranged on the loading side of the machine and designed to activate an opening of the door of the machine for loading.

The pedals according to the invention activate the control unit. Henceforth, a user may actuate a pedal to activate the opening of the door of the machine from the loading side or unloading side. The control unit, therefore, determines according to the state of the sensors and the washing indicator, if activated opening is possible. If activated opening is possible, the pedal is designed to effect the unlocking of the door allowing an opening of the door on the activated side. If activated opening is not possible, the actuation of the pedal has no effect.

Henceforth, pedals according to the invention not only permit the activation of opening for loading or unloading but also ensure the unlocking of the locking means if activated opening is permitted by the locking means.

The bilateral hinge according to the invention may be of any known type. It may be produced by any type of known bilateral hinge.

However, advantageously a machine according to the invention comprises a frame arranged about said tank, comprising an opening opposite said opening of said tank.

According to this variant and in combination, said door comprises hinge plates arranged laterally on the loading side and on the unloading side of said door of the washing machine.

According to this variant and in combination, said locking means comprise at least two claws carried by the frame and arranged, when the door is in the closed position, respectively opposite a hinge plate of the door arranged on the loading edge of the door and opposite a hinge plate of the door arranged on the unloading edge of the door, each claw being designed:

in one position, known as the locked position, corresponding to said locked state, to block the hinge plate of the door arranged opposite so as to prevent any opening of the door, in one position, known as the released position, corresponding to an unlocked state, to permit a release of said hinge plate of the door arranged on said claw side so as to permit a lateral opening of the door on said claw side.

The frame, the claws and hinge plates of the door make it possible to form the bilateral hinge of the door.

Such a bilateral hinge may comprise a variable number of claws.

According to a variant of the invention, said locking means comprise two series of claws carried by the frame, a first series of claws arranged, when the door is in the closed position, opposite a series of hinge plates of the door arranged on the loading edge of the door; and a second series of claws arranged, when the door is in the closed position, opposite a series of hinge plates of the door arranged on the unloading edge of the door.

Preferably, each series of claws is formed by a pair of claws.

The frame, the claws and the hinge plates make it possible to form the bilateral hinge of the door. The claws may have different shapes.

However, advantageously and according to the invention, each claw comprises two levers respectively provided with two hooks which are joined together and designed to be able to form a claw for clamping a hinge plate of said door and to be able to be separated from one another so as to allow the release of said hinge plate of said door and permit a lateral opening of the door.

According to this variant, each claw comprises two articulated levers provided with two hooks. These two levers are designed to be able to be displaced relative to one another so as to be able to form, according to the position of the first lever relative to the second, either a claw for clamping a hinge plate so as to ensure locking of the door, or an opening of the claw for the release of a door hinge plate. Henceforth, each claw thus formed may be in a first configuration corresponding to said released position and in a second configuration corresponding to said first locked position.

The change of configuration of each of the claws may be provided by any known device designed to displace the levers relative to one another. These displacements may be the result of a manual action performed by an operator or obtained by electrically or mechanically controlled mechanisms.

However, advantageously and according to the invention, each claw comprises two levers mounted on the frame by means of at least two journals which are fixed relative to the frame, known as guide journals and at least one slider which is mobile relative to the frame, known as the displacement slider, said displacement slider being designed to cause the displacement of the levers of said claw in a plane at right angles to said access plane between a retracted position in which the levers maintain the door in a washing position and at least one deployed position in which the levers allow an opening of the door, the door being moved away from the washing tank.

Advantageously and according to the invention, each lever extends in a plane perpendicular to the access plane and comprises an oblong aperture, known as the displacement aperture, extending in a principal direction parallel to said access plane and through which is arranged said displacement slider, and two oblong apertures, known as guide apertures, extending in a principal direction at right angles to said access plane, arranged on both sides of said displacement aperture and through which are arranged said guide journals which are fixed relative to the frame.

Advantageously and according to the invention, said hinge of said door comprises, on each loading and unloading side, a mechanism, known as an eccentric mechanism, comprising a shaft which is parallel to said access plane and designed to be driven in rotation by driving means and at each end of which are arranged two eccentric displacement sliders extending in a direction parallel to the direction of the shaft, each slider passing through said oblong displacement apertures of said levers forming a claw such that the eccentric rotation of said sliders forces a displacement of said claws at right angles to said access plane.

An eccentric mechanism according to the invention makes it possible to ensure a change of position of the claws of the hinge of the machine according to the invention. In particular, an eccentric mechanism according to the invention comprising a shaft, at the ends of which are arranged eccentric displacement sliders, each slider being designed to be housed in a displacement aperture, makes it possible to transform a rotating movement of the shaft into a translatory movement of the claws in a direction perpendicular to the oblong apertures.

According to this variant, in combination and according to the invention, one of the oblong guide apertures for one of the levers, known as the articulated lever, has a lower portion which is inclined relative to the guide aperture of the opposite lever such that the lower portions of these guide apertures are not superposed.

Henceforth, a displacement of these levers into the fully deployed position, resulting from the displacement of the eccentric displacement slider, causes a separation between the two hooks of the two levers due to a mechanical contact between the fixed guide journal passing through this portion of the guide apertures which are not superposed, which permits the release of a hinge plate of the door and permits an opening of the door. The claw is now in said released position.

The combination of the articulated levers, an oblong displacement aperture, oblong guide apertures, guide journals and an eccentric mechanism, makes it possible to produce a claw designed:

in the retracted position, corresponding to said locked position, to block the hinge plate of the door arranged opposite said claw, in a fully deployed position corresponding to said released position, to permit a release of said hinge plate of the door arranged on said claw side so as to permit a lateral opening of the door on said claw side.

Advantageously and according to the invention, the displacement slider is designed to position each claw in an intermediate deployed position, known as the pivoted position, between the retracted position and the fully deployed position, and in which it forms a pivot pin of said hinge plate of the door arranged on the side of the claw so as to permit a lateral opening of the door on the opposing side.

As each claw is designed to form a pivot pin, the series of claws arranged on the loading side of the machine is capable of forming a pivot axis of the door to allow an opening of the door on the unloading side, and the series of claws arranged on the unloading side of the machine is designed to form a pivot axis of the door to allow an opening of the door on the loading side.

In this pivoted position, the door is held at a distance above the tank by means of the claws. As the door is no longer in close contact and sealed contact with the tank, it is designed to pivot about one of the pivot axes formed by the claws without risking damaging the tank.

The arrangement of the claws on the frame is preferably determined so that the two loading and unloading pivot axes thus produced are parallel to one another, on both sides of the tank.

Henceforth, according to this variant of the invention, the displacement slider is designed to position each claw:

in said retracted position in which the hinge plate of the door arranged opposite said claw is blocked, in said pivoted position in which it forms a pivot pin of said hinge pin of the door arranged on said claw side so as to facilitate the lateral opening of the door on the opposing side, in said fully deployed position in which it permits a release of said hinge plate of the door arranged on said claw side so as to permit a lateral opening of the door on said claw side.

According to the invention, the position of the eccentric displacement slider dictates the position of the claws. According to one embodiment of the invention, the eccentric mechanism is designed to ensure that the claw passes from the locked position, i.e. from the retracted position, into the pivoted position, i.e. into the intermediate position, when the eccentric displacement slider has carried out a rotation of 130°. Similarly, the eccentric mechanism is designed to ensure that the claw passes from the pivoted position, i.e. from the intermediate position, into the unlocked position, i.e. the fully deployed position, when the eccentric displacement slider has carried out an additional rotation of 30°.

The eccentric mechanisms according to the invention may be of any type.

However, advantageously and according to the invention, said means for driving said shafts of said eccentric mechanisms in rotation comprise electric motors.

These electric motors may be activated by the actuating pedals arranged on the loading side and on the unloading side.

The actuation of the eccentric mechanisms by means of the pedals facilitates the operations for changing the state of the locking means, in particular by an operator who carries in his or her arms medical and/or surgical instruments to be washed which the operator has to arrange in the washing tank.

Advantageously, a machine according to the invention comprises positioning sensors for each claw so as to be able to determine the position of the door of the washing machine.

Advantageously, a machine according to the invention comprises two telescopic articulated arms arranged between the lateral edges of the door and the machine and designed to be able to be deployed as required to ensure automatic opening of the door and to be able to be retracted as required to allow a closing of the door.

Preferably, the activation of the telescopic arms is controlled by the actuating pedals and subject to the authorization of the control unit.

The invention further relates to a machine for washing medical and/or surgical instruments characterized in combination by all or some of the features mentioned above or below.

Figure 3:
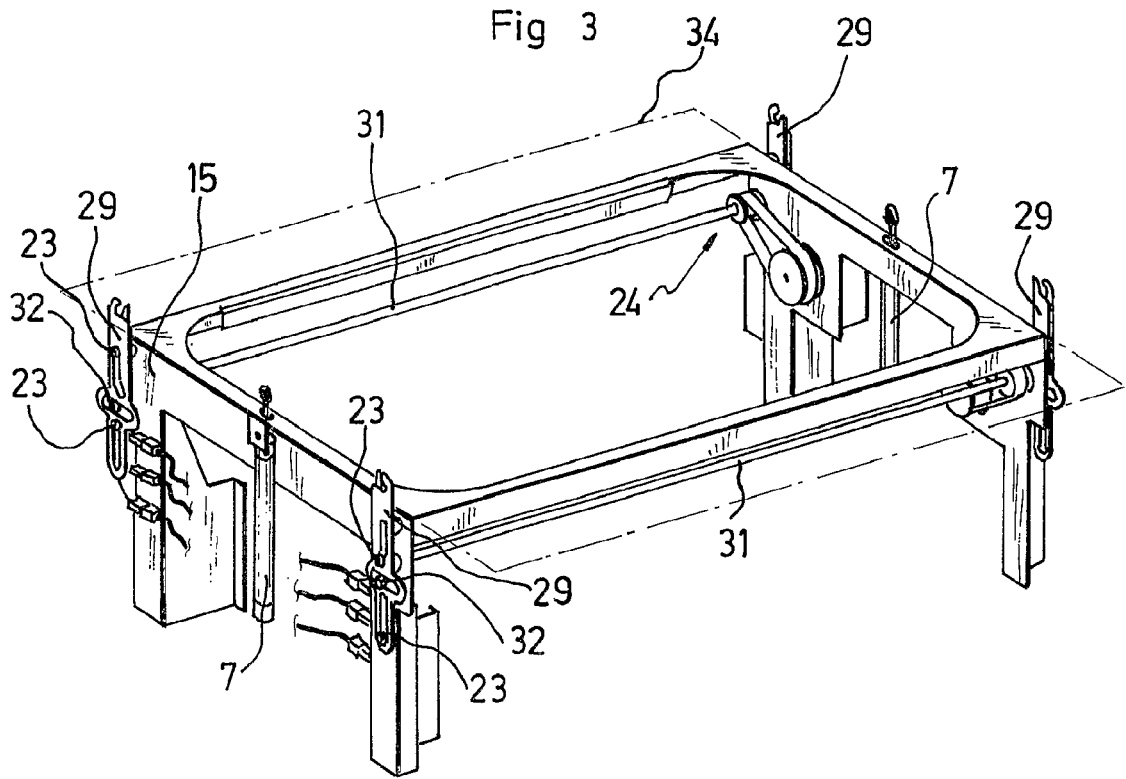
Figure 4:
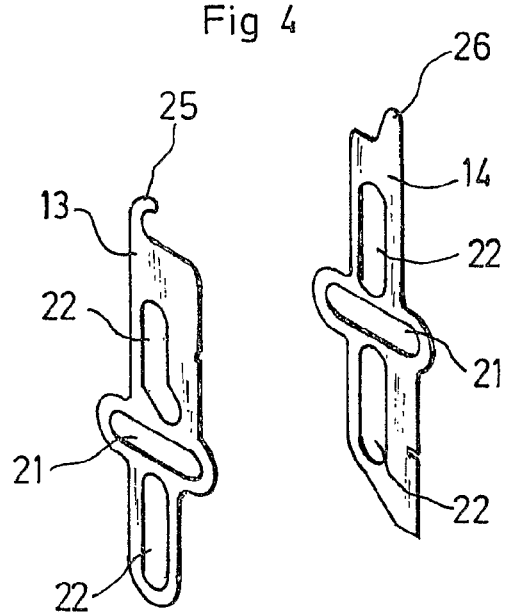
Figure 5A:
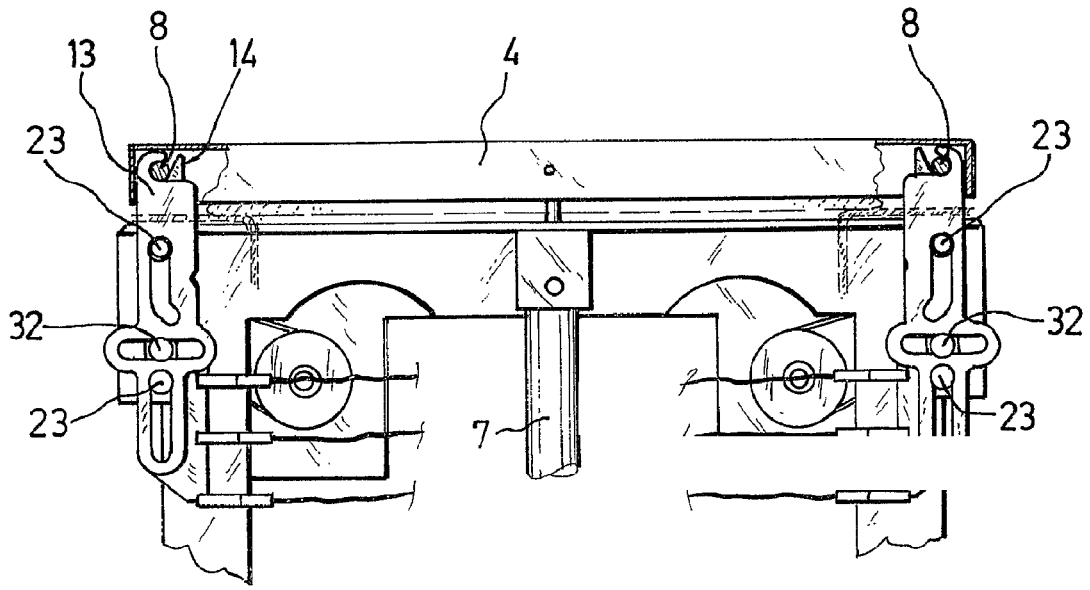
Figure 5B:
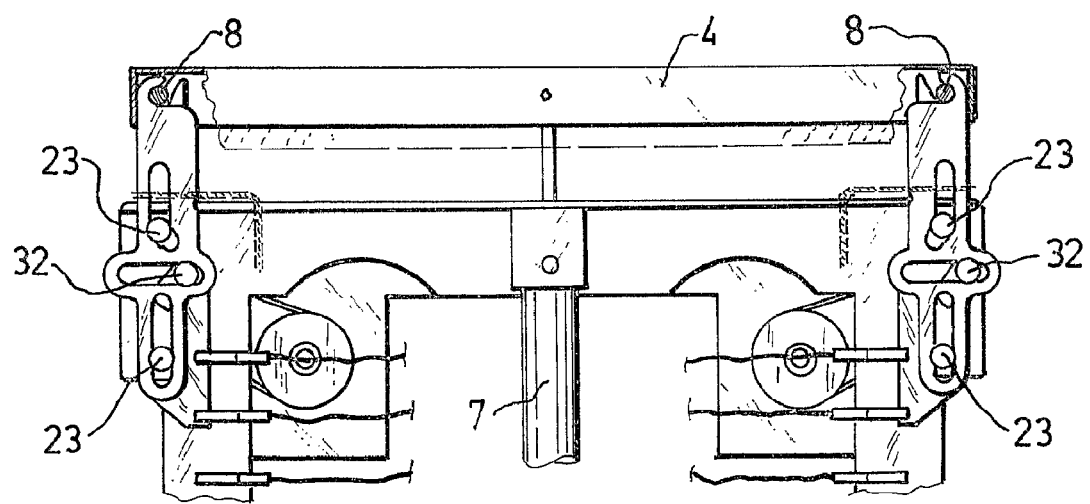
Figure 5C:
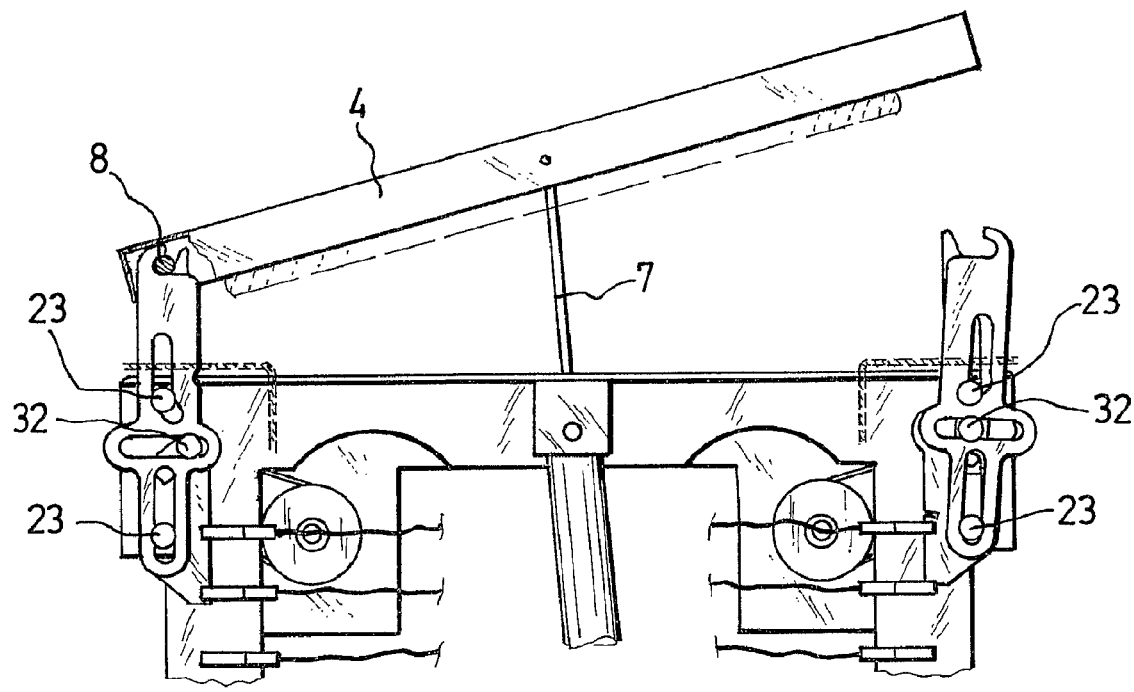
Figure 6:
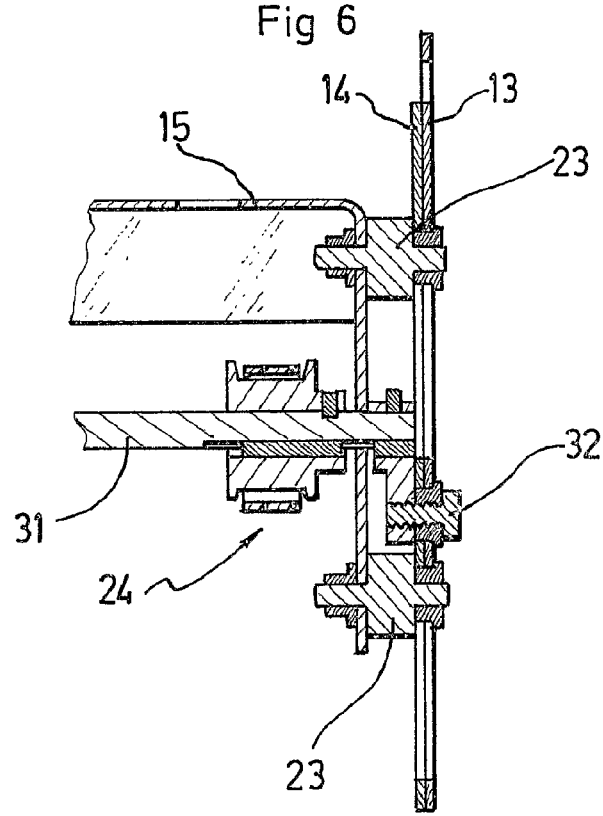

Further features, objects and advantages of the invention will appear from reading the following description which illustrates an embodiment of the invention by way of non-limiting example, with reference to the accompanying drawings; in which:

FIG. 1 is a schematic perspective view of a machine for washing medical and/or surgical instruments according to an embodiment of the invention, FIGS. 2a and 2b are schematic perspective views of a machine for washing instruments for medical and/or surgical use provided with a bilateral door according to one embodiment of the invention, shown respectively in an open position for loading instruments to be washed and in an open position for unloading washed instruments, FIG. 3 is a schematic perspective view of a frame of a hinge of a door of a machine for washing instruments for medical use, according to an embodiment of the invention, FIG. 4 is a schematic exploded perspective view of a claw for locking a door of a machine for washing equipment for medical use according to an embodiment of the invention, FIGS. 5a, 5b and 5c are schematic views from the side of the different positions adopted by the claws for locking a door of a machine for washing instruments for medical and/or surgical use according to an embodiment of the invention, FIG. 6 is a schematic view in section of an eccentric mechanism for driving a claw for locking a machine for washing instruments for medical and/or surgical use according to one embodiment of the invention.

FIG. 1 is a schematic view of a machine for washing instruments 1 for medical and/or surgical use comprising a washing tank 2, defined by walls 3 and comprising an opening for access to the washing tank 2 which extends in a plane, known as the access plane 34.

According to the embodiment of the figures, the access plane 34 is horizontal. However, according to other variants, the access plane 34 may be vertical, or even oblique.

The instruments 1 for medical and/or surgical use are typically fibroscopes, endoscopes, echocardiographic probes, echographic probes, and any other instrument, in particular of the thermolabile type, which require meticulous washing before each use on a patient.

A washing machine according to the invention comprises a door 4 mounted opposite the opening of the washing tank 2. This door 4 is designed to pass from a position, known as the washing position, in which it sealingly covers said opening of said washing tank 2 so as to permit a washing cycle, into at least one position, known as the open position, in which it permits access to the washing tank 2, to load instruments 1 to be washed and/or to unload washed instruments 1. FIG. 1 shows the door 4 in the open position.

As mentioned above, according to the embodiment of the figures, the access plane 34 is horizontal such that in the closed position, the door 4 extends in a horizontal plane. There is nothing to prevent, however, envisaging other configurations, in particular a configuration in which the access plane 34 is vertical, such that the door 4 might extend in the closed position in a vertical plane.

According to one particularly advantageous embodiment, the door 4, the tank 2 and the machine are produced such that in the closed position the door 4 is in the same plane as the external housing of the machine, i.e. once the door is closed, no element may project from the machine, such that an operator may easily and quickly detect a door which is firmly closed and locked in the washing position and a door which is not correctly closed.

The seal between the tank 2 and the door 4 may be obtained by any of the known means. This seal is, for example, obtained by sealing gaskets, for example made of rubber or silicone resin, arranged on the periphery of the face of the door opposite the tank 2 in the closed position, known as the internal face 28, such that when the door 4 is in the closed position, said seals made of rubber or silicone resin may be squashed between the door 4 and the upper edges of the tank 2.

A machine according to the invention comprises means for locking in at least two states of said door 4, a locked state in which said locking means are designed to lock said door 4 in the washing position so that it is impossible to open said door 4 during a washing cycle, and an unlocked state in which said locking means are designed to allow an opening of said door 4.

Said locking means may be of any type. They may be formed by systems comprising a lock, bolt, latch, etc.

According to the embodiment of FIG. 1, said locking means are formed by controlled claws 29 designed to be able to clamp the hinge plates 8 arranged on said internal face 28 of the door 4 and to be able to release said hinge plates 8.

According to the embodiment of the figures, each hinge plate 8 is formed by a metal cylinder extending in a direction parallel to the plane of the door 4, over a length in the order of 1 cm, connected to the internal face 28 of the door 4, by cross members arranged at each of the ends of the cylinder or fixed to the internal face 28 by soldering or welding between the internal face 28 and the cylinder, to achieve this the ends of the cylinder having a greater diameter than the diameter of the central part of the cylinder intended to be clamped by a hinge plate 8. Each hinge plate 8 is arranged on the door 4 so that it is opposite a claw 29 when the door 4 is closed.

A washing machine according to the invention comprises, associated with the locking means, a control unit 16 designed to control the locking means. This control unit 16 may be associated with a programmable controller implemented by electric and/or computerized and/or pneumatic and/or hydraulic means, etc. In particular, such a controller may be provided with a personal computer, may comprise a microprocessor, a control interface, a software package, etc.

A control unit 16 according to the invention is advantageously associated with at least one positioning sensor for said door, known as the door sensor 17, designed to detect an open position of said door 4 and a closed position of said door, at least one sensor for detecting the presence of medical and/or surgical instruments in said tank, known as the tank sensor 18, and at least one washing indicator 19 in two states, a washed state corresponding to the end of a washing cycle, and a state to be washed, corresponding to a washing cycle to be carried out.

FIG. 1 shows schematically the connections between the different sensors and indicator, and the control unit 16.

A door sensor 17 according to the invention and a tank sensor 18 according to the invention may be contact sensors, optical sensors, magnetic sensors, etc.

Advantageously, a tank sensor 18 according to the invention is associated with means for recognizing instruments 1 accommodated in the tank 2. These recognition means may be of any type known per se. They preferably comprise (optical and/or magnetic and/or electric and/or radio frequency and/or mechanical) means for scanning information carried by each instrument. These recognition means are, for example, optical scanning means designed to scan an identification mark arranged on a medical and/or surgical instrument 1 loaded in the tank, so that said sensor may transmit to the control unit 16 information relative to the type of instrument loaded in the machine. This identification mark comprises, for example, a bar code and the optical scanning means comprise known means for scanning a bar code.

According to a further embodiment of the invention, the means for recognizing instruments 1 accommodated in the tank 2 associated with the tank sensor 18 comprise means for remotely scanning electronic radio frequency identification chips (RFID) arranged on an instrument 1 accommodated in the tank 2 and designed to store information relative to this instrument, and to transmit this information to the scanning means. Such means permit an automatic and systematic recognition of the instrument without any specific action.

Such a tank sensor 18 makes it possible, for example, to adapt the type of washing to the type of instrument accommodated in the machine identified by the recognition means.

According to an advantageous embodiment of the invention, the control unit 16 is designed to control the locking of said locking means if, at least simultaneously, said door sensor 17 detects a closed door 4, said tank sensor 18 detects instruments 1 in said washing tank 2 and said washing indicator 19 indicates said state to be washed.

Moreover, the control unit 16 is advantageously designed to change the state of said washing indicator 19 from the washed state to the state to be washed if said tank sensor 18 no longer detects instruments 1 in said washing tank 2.

A washing indicator 19 according to the invention may comprise a digital indicator associated with a standard central memory which the control unit 16 interrogates to determine the state thereof and modifies to change the state thereof. This indicator 19 may also comprise an illuminated indicator visible from the exterior of the machine so that an operator may determine the state of this indicator.

A washing machine according to the invention also comprises a circuit for supplying washing compounds to the machine, opening out into the washing tank. This circuit, known per se, is not shown in the figures for reasons of clarity.

As shown in FIGS. 2a and 2b, the door 4 is mounted on a hinge designed to allow two separate openings.

It is noteworthy in FIGS. 2a, 2b and 1, that claws forming the pivot axis of the door are not shown for reasons of clarity.

The door 4 is mounted on a hinge, known as a bilateral hinge, designed on the one hand to allow a first lateral opening of the door 4 on a first side, known as the loading side 5 of the tank—in particular of the machine—and on the other hand, to allow a second lateral opening of the door on the opposing side, known as the unloading side 6 of the tank—in particular of the washing machine.

FIG. 2a is a view of the machine provided with a door 4 mounted on a bilateral hinge and open on the loading side 5 so as to permit the loading of instruments 1 in the machine and FIG. 2b is a view of the same machine of which the door 4 is open on the unloading side 6 so as to permit the unloading of washed instruments 1.

The passage of the door 4 from the closed position into the open position on the unloading side 6 is only possible if the washing indicator 19 indicates said washed state.

The washing indicator 19 passes from the state to be washed to the washed state, as soon as a washing cycle is finished in a normal manner. The different steps of a washing cycle and means for controlling the execution of each of the steps are not disclosed and are known for the majority of washing machines.

According to the invention, if a cycle has not been correctly carried out, or if an operator decides to suspend the execution of a cycle, the washing machine may only be opened on the loading side of the machine.

According to one embodiment of the invention, the machine is also provided with a system for scanning an identification mark of a user and which is designed to authorize or not the starting or stopping of the machine. This identification mark may be implemented by any known means, in particular by a magnetic card, by a chip card with or without contact (RFID), by entering a code on a keyboard of the machine, by optical scanning of a bar code, etc.

In the embodiment shown in FIGS. 2a and 2b, the door 4 has a parallelepiped shape designed to cover the access opening of the tank 2, which has, according to the embodiment of the figures, a generally rectangular opening. The door 4 is planar and is formed from a rigid material. According to further embodiments, the tank 2 and the door 4 may have other shapes. The door 4 has larger dimensions than the dimensions of the access opening of the tank 2 so that it may cover entirely the access opening of the tank 2 with the purpose of authorizing washing of the instruments 1 accommodated in the tank 2.

According to the embodiment of the figures, the door 4 is defined by a loading edge 10, an opposing unloading edge 11 parallel to the loading edge 10, and two edges, known as lateral edges 12, at right angles to the loading edge 10 and to the unloading edge 11. The loading edge 10 is an edge designed to be articulated on the loading side 5 of the machine and the unloading edge 11 is an edge designed to be articulated on the unloading side 6 of the machine.

According to the invention, each loading edge 10 and unloading edge 11 of the door 4 is provided with two hinge plates 8.

Each hinge plate 8 is designed to be clamped by a claw 29 disclosed below. These claws 29 form the locking means of the door 4.

According to the embodiment, disclosed below, the hinge plates 8 of the same edge extend in the same direction, parallel to the direction in which the hinge plates 8 of the opposing edge extend and parallel to the access plane 34, once the door 4 is in the closed position.

These claws 29 are fixed to a frame 15, such as shown in FIG. 3. The frame 15 of the hinge is arranged about the tank 2 and comprises lateral walls and an opening opposite the tank opening 2.

According to the embodiment of the figures, two pairs of claws 29 are carried by the frame 15 and are arranged, when the door 4 is in the closed position, so as to be respectively opposite a pair of hinge plates 8 of the door 4 arranged on the loading edge 10 and a pair of hinge plates 8 of the door arranged on the unloading edge 11 of the door.

The pair of claws 29 arranged on the loading side 10 of the machine is designed to form, when each claw 29 of this pair of claws 29 is in the pivoted position, a pivot axis of the door to permit an opening of the door 4 on the unloading side 6, and the pair of claws 29 arranged on the unloading side 6 of the machine is designed to form a pivot axis of the door 4 when opening the door 4 on the loading side 5.

These pivot axes are parallel to one another and parallel to the access plane 34 and are embodied in the figures by the shafts 31.

Each claw 29 is capable in a first position known as the locked position, of blocking the hinge plate 8 of the door 4 arranged opposite; in a second position, known as the released position, of permitting a release of said hinge plate 8 of the door 4 arranged on the side of this claw 29, so as to permit a lateral opening of the door 4 on the side of this claw; and in a third position, known as the pivoted position, of forming a pivot pin of said hinge plate 8 of the door 4 arranged on the side of the claw so as to permit a lateral opening of the door 4 on the opposing side.

To achieve this, a claw 29 according to the invention comprises, as shown in FIG. 4, two levers 13, 14 joined together. The lever 13 comprises at one of its ends, a hook 25 designed, in cooperation with a hook 26 arranged at one end of the joined lever 14, to form a claw for supporting a hinge plate 8 of a door 4 when the two levers 13, 14 are superposed on one another. The pivoting of one lever relative to the other permits a separation of the hooks from one another and a release of a hinge plate 8 blocked between the hooks.

This pivoting of one lever relative to the other is implemented by the combination of structures of the levers disclosed below and at least one mechanism, known as the eccentric mechanism, disclosed below.

Each lever has the general shape of a plate extending at right angles to the access plane 34 and to the pivot axis formed by each pair of claws 29.

Each lever comprises an oblong aperture, known as the displacement aperture 21, extending in a direction parallel to said access plane 34, once the claw 29 is mounted on the frame 15.

Each lever also comprises two oblong apertures, known as guide apertures 22, perpendicular to the displacement aperture 21. Preferably, the guide apertures of each lever are arranged on both sides of the displacement aperture 21.

Each displacement aperture 21 of each lever makes it possible to displace said lever perpendicular to said displacement aperture 21.

To achieve this, the frame 15 carries mechanisms, known as eccentric mechanisms 24, designed to ensure said displacement of the levers.

Each eccentric mechanism 24 comprises, as shown in particular in FIG. 6, a shaft 31, extending parallel to said access plane 34 and at each end thereof is arranged a slider 32 which is eccentric relative to the shaft 31 and parallel to the shaft 31.

Each shaft 31 is connected to means for driving this shaft 31 in rotation. These means for driving in rotation may be of any type, mechanical, electrical, hydraulic etc. According to the embodiment of the figures, these means for driving in rotation are associated with electric motors.

The rotation of a shaft 31 causes the rotation of the eccentric sliders 32. Each eccentric slider 32 passes through the displacement apertures 21 of the levers 13, 14 forming a claw 29.

Moreover, the frame 15 comprises journals 23 fixed to the frame and designed to be housed in the guide apertures 22 of the levers 13, 14.

Henceforth, the rotation of an eccentric slider 32 about the shaft 31 forces and drives the displacement of each lever according to the direction of the guide apertures.

The length of at least one of the guide apertures 22 is selected so that during the displacement of the levers 13, 14 perpendicular to said access plane 34, at least one journal 23 is in mechanical contact with the lower end of a guide aperture 22.

Thus according to the invention, this guide aperture 22 of one of the levers, known as the articulated lever 13, has a lower portion which is inclined relative to the direction of the guide aperture of the superposed lever 14. In such a manner, during the displacement of the levers 13, 14 guided by said guide journal 23, the end of travel of said guide journal 23 in the guide apertures which are not superposed, causes a pivoting of the lever 13 which is articulated relative to the lever 14. This pivoting causes a separation of the two hooks 25, 26 of the two levers 13, 14 from one another and permits the release of a hinge plate 8 of the door beyond the claw 29, said claw 29 now being in the released position.

The combination of the guide journals 23, guide apertures 22, eccentric mechanisms 24, displacement apertures 21 and levers 13, 14 makes it possible to produce means for locking a door, designed in a first position, to block the hinge plate 8 of a door 4 and in a second position, to permit a release of a hinge plate 8 of a door 4.

Moreover, the combination of articulated levers 13, 14, an oblong displacement aperture 21, oblong guide apertures 22, guide journals 23 and an eccentric mechanism 24, makes it possible to produce a claw 29 designed:

in a retracted position, corresponding to said locked position, to block the hinge plate 8 of the door 4 arranged opposite said claw 29, in a fully deployed position corresponding to said released position, to permit a release of said hinge plate 8 of the door 4 arranged on said claw side so as to permit a lateral opening of the door 4 on said claw 29 side.

During the travel of the guide apertures about the fixed guide journal, the hooks of the levers 13, 14 remain closed whilst there is no contact between the guide journal and inclined portion of the apertures.

Henceforth, advantageously, this position is denoted, for example by positioning sensors, as being a position known as the pivoted position.

In this pivoted position, the door 4 is held in suspension above the tank 2 by means of the claws 29. As the door is no longer in close and sealed contact with the tank it is capable of pivoting about one of the pivot axes formed by the claws 29 without risking damaging the tank.

Henceforth, the displacement of the displacement slider 32 is designed to position each claw 29 in a retracted position in which the two levers 13, 14 form a claw for supporting the hinge plate 8 arranged opposite; in a position known as the pivoted position, in which the levers form a pivot pin of a door, the door being raised relative to its washing position; a fully deployed position in which the levers 13, 14 are pivoted relative to one another such that the hooks 25, 26 arranged at their ends are separated from one another and permit the release of a hinge plate of the door beyond the claw 29.

The actuation of the eccentric mechanisms 24 causes the displacement of the levers and thus determines the position of the claws 29 forming the locking means.

The first position, known as the locked position, shown in FIG. 5a, corresponds to a position of the eccentric mechanism 24 in which the eccentric slider 32 holds the claw 29 in the retracted position.

The second position, known as the released position, shown in FIG. 5c, corresponds to a position of the eccentric mechanism 24 in which the eccentric slider 32 has performed a rotation of 160 degrees relative to the first position about the shaft 31 and brings the claw 29 into the fully deployed position.

The third position, known as the pivoted position, shown in FIG. 5b, corresponds to a position of the eccentric mechanism 24 in which the eccentric slider 32 has performed a rotation in the order of 130 degrees relative to the first position about the shaft 31 and brings the levers into an intermediate position between the retracted position and the fully deployed position.

Thus in normal operation, the actuation of the eccentric mechanism permits the passage from the locked position to the pivoted position, and then to the released position.

According to one advantageous embodiment of the invention, the means for driving the eccentric shafts in rotation are actuated by pedals. The machine thus comprises a pedal, known as the unloading pedal, arranged on the unloading side 6 of the machine and designed to activate an opening of the door for unloading and a pedal, known as the loading pedal 45, arranged on the loading side 5 of the machine and designed to activate an opening of the door of the machine for loading.

In the event of a machine with a plurality of tanks, the machine preferably comprises one loading pedal per tank and one unloading pedal per tank. However, in the case of a machine with a plurality of tanks operating in a synchronous manner, the machine may comprise a single pedal for unloading and a single pedal for loading.

The control unit 16 thus determines if the action which has been activated may be fulfilled, depending on the state of the sensors of the machine.

According to this embodiment, the control unit 16 authorizes opening for loading the machine if no washing cycle is underway, if the tank sensor 18 indicates that the tank 2 is empty, and if the pedal 45 for loading the machine is actuated.

According to this embodiment, the control unit 16 allows opening for unloading if the washing indicator 19 indicates a washed state, if the tank sensor 18 indicates the presence of an instrument in the tank 2 and if the unloading pedal has been actuated.

According to this variant, the identification of a user authorized by the identification means may also be a condition for the opening for unloading.

According to an advantageous embodiment of the invention, the loading and unloading pedals are also designed to activate the closure of the door. To achieve this, an operator has to actuate the pedal arranged on the side where the door is open.

According to the invention, the control unit is designed to allow, at any given moment, only one single action. The latter depends, as mentioned above, on the state of the sensors (position of the door, instruments in the tank, authorized user), the washing indicator and control pedals.

According to an advantageous embodiment of the invention, the door 4 is also articulated about two telescopic articulated arms 7 arranged between the lateral edges 12 of the door 4 and the frame 15 of the machine.

Each articulated arm 7 forms a pivot connection with the door 4. This pivot connection is preferably arranged in the middle of the lateral edge 12 so that the door may pivot about this pivot connection when opening for loading and when opening for unloading. Preferably, each articulated arm 7 also forms a pivot connection with the frame 15. The pivot axes of these different pivot connections are parallel and preferably parallel to the pivot axes of the door implemented by the claws 29.

According to a particularly advantageous embodiment of the invention, the articulated arms 7 are actuators designed to be deployed as required by the control unit 16. The deployment of the arms 7 is only authorized if the locking means are in an unlocked state for loading or unloading. In contrast, the arms 7 have to be retracted so that the locking means may lock the door 4 in the washing position.

Preferably, the actuators are pneumatic cylinders, so that the passage of the door from the closed position to the open position may be carried out by pressurizing the actuators, and so that the passage of the door from the open position to the closed position may be implemented by evacuating the actuators by means of an exhaust valve, which causes the closure of the door due to the natural phenomenon of gravity.

Henceforth, the control unit 16 controls the locking means and activates the displacement of the articulated arms when the locking means are in the corresponding state.

According to one advantageous embodiment combining the different embodiments disclosed, the passage of the door from the closed locked position to, for example, an open unloading position, involves sequentially: an actuation of the pedal arranged on the unloading side, an authorization for opening provided by the control unit (which depends on the state of the sensors of the tank, door and washing indicator), activation of the electric motors of the eccentric mechanisms to position the claws in the corresponding position and supplying power to the pneumatic cylinders.

According to this summary, all the claws 29 are initially in the retracted position corresponding to the locked position. The activation of the electric motors of the eccentric mechanisms causes the rotation of the eccentric sliders 32 which cause the displacement of all the claws 29 from the retracted position to the intermediate position. The hinge plates 8 of the door 4 are thus always captured in the claws 29, but the door 4 is no longer in close contact with the upper edge of the tank 2. A pivoting of the door about the pivot axis formed by the claws 29 is now possible. The electric motor of the eccentric mechanism 24 arranged on the unloading side 6 continues the driving in rotation of its associated eccentric sliders 32. Said eccentric sliders thus cause the displacement of the claws 29 arranged on the unloading side 6 in the fully deployed position, corresponding to a released position. The door 4 is thus designed to be open on the unloading side 6. The control unit 16 is now able to allow the actuation of the actuators forming the telescopic arms 7. The deployment of the arms 7 ensures the opening of the door 4 on the unloading side 6.

The passage of the door from the locked position to the open position for loading is carried out in a similar manner, with the difference that once in the intermediate position, it is the eccentric mechanism arranged on the loading side which continues the driving in rotation of its eccentric sliders.

The passage of the door from an open position, for example for loading, to the closed locked position involves sequentially: an actuation of the loading pedal, an authorization for closure provided by the control unit, an evacuation of the pneumatic cylinders so as to permit the closure of the door by gravity, a detection of the intermediate position of the door, and an activation of the electric motors of the eccentric mechanisms to position the claws in the locked position.

According to this summary, the evacuation of the actuators causes the passage of the door 4 from the open position to a position in which it covers the tank 2. As the claws 29 on the loading side 5 are open, they receive the hinge plates 8 of the door 4 arranged opposite. The activation of the motor of the eccentric mechanism 23 on the loading side 5 makes it possible by means of the associated eccentric sliders 32, to reclose the claws 29 on the loading side 5, so that all claws 29 are in the intermediate closed position. The eccentric mechanisms 23 of the two sides of the machine are thus activated to move each claw 29 from its intermediate position to the position corresponding to the locked position of the door 4.

The invention is not limited solely to the embodiments disclosed. In particular, a washing machine according to the invention may have a different structure and may be provided with monitoring and controlling means which complement the purpose of responding to the specific requirements for certain medical and/or surgical instruments.

A machine according to the invention may also be programmed so as to behave as a machine with one door and with one possible opening side per door.

A machine according to the invention may, in particular, comprise a plurality of tanks, each being provided with a bilateral door according to the invention. The tanks may operate in a synchronous or an asynchronous manner. The tanks may be arranged in a row so as to define an unloading side of the machine and a loading side of the machine. They may be arranged according to different configurations without departing from the scope of the invention.

The invention claimed is:

1. A machine for washing medical and/or surgical instruments comprising:
    at least one washing tank designed to receive medical and/or surgical instruments, said tank being defined by walls and comprising an opening for access to the tank for loading instruments to be washed into the tank or for unloading washed instruments from the tank, said opening extending into a plane, known as the access plane,
    a door arranged opposite said opening of said washing tank, said door being mounted on the machine so as to be able to pass from a position, known as the washing position, in which it sealingly covers said opening of said washing tank so as to permit a washing cycle, into at least one position, known as the open position, in which it permits access to the washing tank to load the instruments to be washed or to unload the washed instruments, wherein said door is mounted on a hinge, known as a bilateral hinge, designed to allow a first lateral opening of the door, known as the opening for loading, on a first side, known as the loading side of the machine, in which said door permits access to said tank from said loading side and prevents access to said tank from the opposing side, and to permit a second lateral opening, known as the opening for unloading, on the opposing side, known as the unloading side of the washing machine, in which said door permits access to said tank from said unloading side and prevents access to the tank from said loading side, the machine further comprising:
 a pedal, known as the unloading pedal, arranged on the unloading side of the machine and designed to activate an opening of the door for unloading and a pedal, known as the loading pedal, arranged on the loading side of the machine and designed to activate an opening of the door for loading.

2. The machine as claimed in claim 1, wherein it comprises two controlled telescopic articulated arms arranged between the lateral edges of the door and the machine, said articulated arms being designed to be deployed to ensure automatic opening of the door and to be able to be retracted to allow a closing of the door.

3. The machine as claimed in claim 1, wherein said door is designed to extend vertically in the closed position, in a horizontal plane parallel to the plane of the opening, and in that said bilateral hinge is arranged such that said loading and unloading apertures of said door are openings at the top of said tank.

4. The machine as claimed in claim 1, wherein it comprises:
 means for locking said door in at least two states, a locked state in which said locking means are designed to lock said door in the washing position such that it is impossible to open said door during a washing cycle, and an unlocked state in which said locking means are designed to allow an opening of said door,
 a control unit for said locking means designed to be able to control the locking and unlocking of the locking means.

5. The machine as claimed in claim 4, wherein said control unit is designed to:
 control the locking of said locking means if at least said door sensor detects a closed door, said tank sensor detects instruments in said tank and said washing indicator indicates said state to be washed,
 control the unlocking of said locking means in the other cases.

6. The machine as claimed in claim 4, wherein it comprises, associated with said control unit:
 at least one positioning sensor for door, known as a door sensor, designed to detect an open position of said door and a closed position of said door,
 at least one sensor for detecting the presence of medical and/or surgical instruments in said tank known as the tank sensor,
 at least one washing indicator which indicates one of two states, a washed state corresponding to the end of the washing cycle and a state to be washed corresponding to a washing cycle to be carried out or underway.

7. The machine as claimed in claim 6, wherein said control unit is designed to:
 control the passage of the locking means into the unlocked loading state if at least said tank sensor detects an absence of instruments for washing and a door sensor detects a closed door,
 control the passage of the locking means into the unlocked unloading state if at least said washing indicator indicates said washed state and a door sensor detects a closed door.

8. The machine as claimed in claim 4, wherein said control unit is designed to change the state of said washing indicator from the washed state to the state to be washed if at least said tank sensor no longer detects instruments in said washing tank.

9. The machine as claimed in claim 8, wherein said locking means comprise three states, a locked state in which the locking means are designed to lock said door in the washing position, a first unlocked state, known as the unlocked loading state in which the locking means are designed to permit an opening of said door for loading, and a second unlocked state, known as the unlocked unloading state, in which the locking means are designed to permit an opening of said door for unloading.

10. The machine as claimed in claim 4, wherein it comprises a frame arranged about said tank and comprising an opening opposite said opening of said tank and in that said door comprises hinge plates arranged respectively on the edge of the door located on the loading side of the machine, once the door is in the closed position, known as the loading edge, and on the edge of the door located on the unloading side, once the door is in the closed position, known as the unloading edge of the door.

11. The washing machine as claimed in claim 10, wherein said locking means comprise at least two claws carried by the frame and arranged, when the door is in the closed position, respectively opposite a hinge plate of the door arranged on the loading edge of the door and opposite a hinge plate of the door arranged on the unloading edge of the door, each claw being designed:
 in one position, known as the locked position, corresponding to said locked state, to block the hinge plate of the door arranged opposite so as to prevent any opening of the door,
 in one position, known as the released position, corresponding to an unlocked state, to permit a release of said hinge plate of the door arranged on the same side as the claws so as to permit a lateral opening of the door on the same side as the claws.

12. The machine as claimed in claim 11, wherein it comprises positioning sensors for each claw.

13. The machine as claimed in claim 11, wherein each claw comprises two levers respectively provided with two hooks which are joined together and designed to be able to form a claw for clamping a hinge plate of said door and to be able to be separated from one another so as to allow the release of said hinge plate of said door and to permit a lateral opening of the door.

14. The machine as claimed in claim 13, wherein each claw is mounted on the frame by means of at least two journals which are fixed relative to the frame, known as guide journals and at least one slider which is mobile relative to the frame, known as the displacement slider, said displacement slider being designed to cause the displacement of said levers of said claw in a plane at right angles to said access plane between a retracted position in which the levers maintain the door in a washing position, and at least one deployed position in which the levers allow an opening of the door on the same side as the claws, the door being thus moved away from the tank.

15. The machine as claimed in claim 14, wherein each displacement slider is designed to position each claw, in an intermediate deployed position, known as the pivoted position, between said retracted position and a fully deployed position, and in which it forms a pivot pin of a hinge plate of the door clamped in said claw.

16. The machine as claimed in claim 14, wherein each lever extends in a plane at right angles to said access plane and comprises an oblong aperture, known as the displacement aperture, extending in a principal direction parallel to said access plane and through which is arranged, at right angles to said principal direction, said displacement slider and two oblong apertures, known as guide apertures, extending in a direction at right angles to said access plane, arranged on both sides of said displacement aperture and through which are arranged said guide journals which are fixed relative to said frame.

17. The machine as claimed in claim 16, wherein for each claw, one of the guide apertures for one of the levers, has a portion which is inclined relative to the guide aperture of the coordinating lever on the opposite end of the same side of said door.

18. The machine as claimed in claim 16, wherein said bilateral hinge of said door comprises on each loading and unloading side, a mechanism, known as an eccentric mechanism, comprising a shaft which is parallel to said access plane and designed to be driven in rotation by driving means and at each end of which are arranged two eccentric displacement sliders, extending in a direction parallel to the direction of the shaft, each slider passing through said oblong displacement apertures of the levers forming a claw such that the eccentric rotation of said displacement sliders forces a displacement of said claws at right angles to said access plane.

19. The machine as claimed in claim 18, wherein said means for driving said shafts of said eccentric mechanisms in rotation are associated with electric motors.

* * * * *